(12) United States Patent
Adrian et al.

(10) Patent No.: US 7,144,867 B2
(45) Date of Patent: Dec. 5, 2006

(54) ANTICANCER GLYCOSIDE COMPOUNDS

(75) Inventors: Thomas E. Adrian, Chicago, IL (US); Peter D. Collin, Sunset, ME (US)

(73) Assignees: Northwestern University, Evanston, IL (US); Coastside Bio Resources, Stonington, ME (US)

( * ) Notice: Subject to any disclaimer, the term of this patent is extended or adjusted under 35 U.S.C. 154(b) by 93 days.

(21) Appl. No.: 11/044,496

(22) Filed: Jan. 27, 2005

(65) Prior Publication Data

US 2005/0288239 A1 Dec. 29, 2005

Related U.S. Application Data

(60) Provisional application No. 60/539,548, filed on Jan. 27, 2004.

(51) Int. Cl.
*A01N 43/04* (2006.01)
*A61K 31/70* (2006.01)
*A01N 57/00* (2006.01)
*A61K 31/665* (2006.01)

(52) U.S. Cl. .............................. 514/33; 514/35; 514/54; 514/27; 514/99; 514/100

(58) Field of Classification Search ................ 514/33, 514/35, 54, 27, 99, 100
See application file for complete search history.

(56) References Cited

OTHER PUBLICATIONS

Yayli et al. Phytochemistry (1999), vol. 50, pp. 135-138.*

\* cited by examiner

*Primary Examiner*—Patrick Lewis
(74) *Attorney, Agent, or Firm*—Hedlen & Carroll, LLP

(57) ABSTRACT

The present invention relates to new classes of anti-cancer compounds. In particular, the present invention provides glycoside compounds as anti-cancer agent, alone, or in combination with other anti-cancer agents or therapies.

15 Claims, 9 Drawing Sheets

*: Significant inhibition of tube formation (≥30%)

The inhibitory effect of test substances on tube formation in the HUVEC cell angiogenesis assay

ANTICANCER GLYCOSIDE COMPOUNDS

This Application claims priority to provisional patent application Ser. No. 60/539,548 filed Jan. 27, 2004, which is herein incorporated by reference in its entirety.

FIELD OF THE INVENTION

The present invention relates to new classes of anti-cancer compounds. In particular, the present invention provides glycoside compounds as anti-cancer agents, alone, or in combination with other anti-cancer agents or therapies. In particular, the present invention relates to the use of sea cucumber frondosides A and B as anti-cancer agents.

BACKGROUND

While new cancer therapies are continuously being discovered, there remains a great need for new anti-cancer compounds and therapies, particularly for cancers such as pancreatic cancer, which is largely untreatable with current therapies.

Pancreatic cancer is one of the most enigmatic and aggressive malignant diseases facing oncologists (Black et al., Oncology 1996; 10:301–307; Cameron et al., Ann Surg 1993; 217:430–438; Doll et al., BMJ 1976; 2:1525–1536). It is now the fourth leading cause of cancer death in the USA and its incidence has significantly increased over the past 20 years (Black et al., supra; Cameron et al., supra; Doll et al., supra). Pancreatic cancer is characterized by late diagnosis, very poor prognosis and lack of an effective response to conventional therapy. The five year survival rate for this disease is less than 4% and the median survival time after diagnosis is less than 6 months (Silverberg et al., J Am Cancer Society 1990; 40: 9–26; Hunstad et al., Surg Oncol 1995; 4: 61–74; Serafini et al., Cancer Control 2000; 7: 437–444). At present, surgical resection is still the only effective treatment option, but only about 15% of carcinomas of the head of the pancreas are resectable and there are few long-term survivors even after apparent curative resection (Silverberg et al., supra; Hunstad et al., supra; Serefini et al., supra). On the other hand, chemotherapy and radiation therapy provide only limited palliation without meaningful improvement in survival in patients with non-resectable disease (Silverberg et al., supra; Hunstad et al., supra; Serefini et al., supra). Clearly, only new therapeutic strategies can improve on this dismal situation.

SUMMARY OF THE INVENTION

The present invention relates to new classes of anti-cancer compounds. In particular, the present invention provides glycoside compounds as anti-cancer agents, alone, or in combination with other anti-cancer agents or therapies. In particular, the present invention relates to the use of sea cucumber frondosides A and B as anti-cancer agents.

Accordingly, in some embodiments, the present invention provides frondoside (e.g., *Cucumaria frondosa* Frondoside A or Frondoside B) compositions and methods for use in the treatment of cancer and diseases characterized by aberrant angiogenesis. The present invention is not limited to the treatment of a particular cancer. Exemplary cancers that are suitable for treatment with the methods and compositions of the present invention include prostate, breast, pancreatic, skin, and colon cancer.

For Example, in some embodiments, the present invention provides a method for reducing cellular proliferation comprising the step of exposing a Frondoside compound (e.g., *Cucumaria frondosa* Frondoside A or Frondoside B) to cells. In some embodiments, the cellular proliferation is associated with cancer. In some embodiments, the cells are located in vivo in a subject (e.g., a human). In some embodiments, the cancer is pancreatic cancer, breast cancer, colon cancer, skin cancer or prostate cancer. In some embodiments, the Frondoside compound is obtained from a natural source. In some embodiments, the cells are further exposed to a second compound having anti-proliferative properties (e.g., a known cancer chemotherapeutic agent).

The present invention further provides a therapeutic composition comprising a Frondoside compound (e.g., *Cucumaria frondosa* Frondoside A or B) configured for administration to a subject having or suspected of having cancer or diseases characterized by aberrant angiogenesis. In preferred embodiments, the frondoside is formulated as a pharmaceutical composition. In some embodiments, the composition further comprises a second anti-proliferative compound. In some embodiments, the cancer is pancreatic cancer, breast cancer, colon cancer, skin cancer and prostate cancer. In some embodiments, the Frondoside compound is obtained from a natural source. In some embodiments, the subject is a human.

DEFINITIONS

Figure 1:
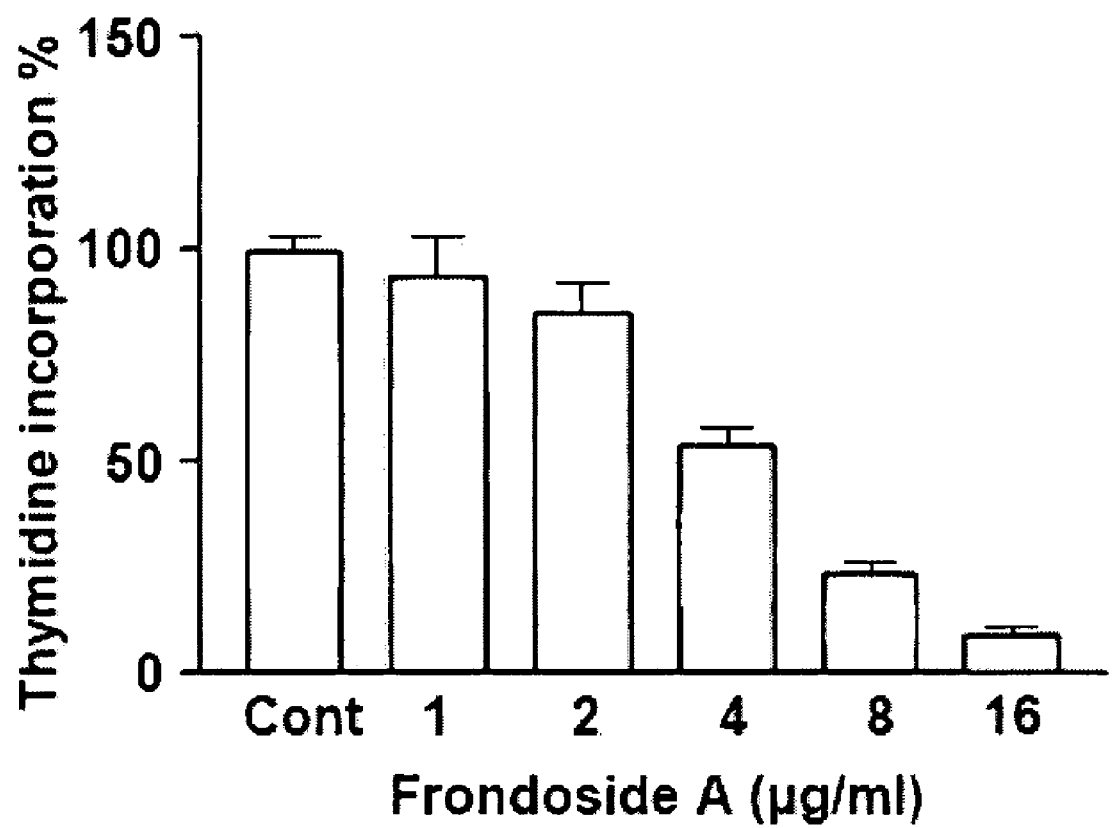
FIG. 1 shows the effect of different concentrations of frondoside A on proliferation of the pancreatic cancer cell line AsPC-1. Results are expressed as % of control. =$P<0.01$; *=$P<0.001$ compared to control.

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass)

or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

As used herein, the term "initial diagnosis" refers to a test result of initial cancer diagnosis that reveals the presence or absence of cancerous cells (e.g., using a biopsy and histology).

As used herein, the term "post surgical tumor tissue" refers to cancerous tissue that has been removed from a subject (e.g., during surgery).

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present invention.

As used herein, the terms "anticancer agent," "conventional anticancer agent," or "cancer therapeutic drug" refer to any therapeutic agents (e.g., chemotherapeutic coumpounds and/or molecular therapeutic compounds), radiation therapies, or surgical interventions, used in the treatment of cancer (e.g., in mammals).

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

The term "derivative" of a compound, as used herein, refers to a chemically modified compound wherein the chemical modification takes place either at a functional group of the compound, aromatic ring, or carbon backbone. Such derivatives include esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

An "effective amount" is an amount sufficient to effect beneficial or desired results. An effective amount can be administered in one or more administrations.

As used herein, the term "administration" refers to the act of giving a drug, prodrug, or other agent, or therapeutic treatment (e.g., radiation therapy) to a physiological system (e.g., a subject or in vivo, in vitro, or ex vivo cells, tissues, and organs). Exemplary routes of administration to the human body can be through the eyes (opthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

"Coadministration" refers to administration of more than one chemical agent or therapeutic treatment to a physiological system (e.g., a subject or in vivo, in vitro, or ex vivo cells, tissues, and organs). "Coadministration" of the respective chemical agents and therapeutic treatments may be concurrent, or in any temporal order or physical combination.

DETAILED DESCRIPTION OF THE INVENTION

The present invention relates to new classes of anti-cancer compounds. In particular, the present invention provides glycoside compounds as anti-cancer agents, alone, or in combination with other anti-cancer agents or therapies. Accordingly, in some embodiments, the present invention provides frondosides (e.g., *Cucumaria frondosa* Frondosides A and B) compositions and methods for using the compositions in the treatment of cancer and other angiogenic diseases.

For example, in some embodiments, the present invention provides frondoside compounds obtained from the natural environment and derivatives thereof having similar biological properties. The present invention is illustrated with the compound Frondoside A obtained from *Cucumaria frondosa*. Frondoside B obtained from *Cucumaria frondosa* also showed anti-cancer activity. However, the present invention is not limited to these particular examples. Skilled artisans will understand that similar compounds isolated from other sources and derivatives of such compounds find use in the present invention.

Sea cucumbers are important components of traditional Chinese medicine. Active compounds isolated from these echinoderms have interesting biological properties and potential clinical use. One group of active compounds are glycosylated triterpenoid saponins, which show anti-cancer activity (Kashiwada et al., J Nat Prod 1997; 60(1):1105–1114; Friess et al., Ann N Y Acad Sci 1960; 17(90):893–901; Pettit et al., J Pharm Sci 1976; 65(10): 1558–1559; Friess et al., J Pharm Exp Ther 1959; 126: 323–329; Kuznetsova et al., Comp Biochem Physiol C 1982; 73(1):41–43; Zou et al., J Nat Prod 2003; 66(8): 1055–1060). However, many glycoside anti-cancer agents are 'cytotoxic' by necrosis, rather than apoptosis. One such compound is frondoside, which is a glycoside derived from the Atlantic sea cucumber, *Cucumaria frondosa*, a species that is very abundant on the North Atlantic Coast of America. The effects of this agent on proliferation and apoptosis of cancer cells have not previously been reported.

Experiments conducted during the course of development of the present invention tested a series of concentrations of frondoside A ranging from 1 µg/mL to 32 µg/mL for anti cancer activity against pancreatic, prostate and colon cancer cell lines. The results showed that concentrations higher than 16 µg/mL frondoside A caused immediate necrosis of cells, indicating a cytotoxic effect at these high concentrations. Therefore, concentrations between 1 µg/mL to 16 µg/mL frondoside A were used for subsequent experiments on induction of apoptosis in pancreatic cancer cells, to avoid cytotoxicity. At low concentrations, frondoside A inhibited growth and induced apoptosis in concentration-dependent manner in AsPC-1 cell. Because 4 µg/mL frondoside A reduced incorporation of $^3$H-methyl thymidine into DNA by approximately 50% within 24 hours, the effect of this concentration on cell number over a prolonged time period from 24 to 72 hours was tested. The results showed profound inhibition of growth that is time-dependent. The cyclin dependent kinase inhibitor, p21 mediates cellular responses to DNA-damaging agents (Waldman et al., Cancer Res 1995; 55: 5187–5190). The present studies revealed a marked time-dependent increase in expression of p21 in response to frondoside, while expression of P27 protein was not changed. The present invention is not limited to a particular mechanism. Indeed, an understanding of the mechanism is not necessary to practice the present invention. Nonetheless, it is contemplated that these results suggest that the p21 protein might play role in the growth inhibition of pancreatic cancer cells, induced by frondoside A.

The inhibitory effect of frondoside A on pancreatic cancer cell growth was confirmed in the athymic mouse xenograft model. A very low concentration of frondoside caused a substantial inhibition of tumor growth throughout the period of study.

Morphological changes are characteristic features of cells undergoing apoptosis and these are readily observed microscopically. Specific apoptotic morphological changes were identified following frondoside A treatment within 48 hours and the proportion of apoptotic cells increased with the time of treatment. To confirm the effect of frondoside A on apoptosis in pancreatic cancer cells, annexin V staining and TUNEL assay were carried out. During early apoptosis, phosphatidylserine, a phospholipid usually located on the inner surface of plasma membrane, translocates to the outer plasma membrane. Annexin V preferentially binds to negatively charged phosphatidylserine. By conjugating fluorescein to annexin V, it can be used to identify early apoptosis by flow cytometry or fluorescence microscopy. Annexin V was binds to early apoptotic cells, but they do not exhibit intracellular staining with propidium iodide. As the cells progress through apoptosis, the integrity of the plasma membrane is lost, allowing propidium iodide to penetrate and label the cells with a strong yellow-red fluorescence. The results showed strong annexin V staining in AsPC-1 cell after frondoside A treatment for 3 hours, but no staining in control untreated cells. In the late stages of apoptosis, genomic DNA is cleaved in fragments due to activation of endonucleases. The TUNEL assay identifies these DNA fragments in apoptotic cells by use of a fluorescent indicator to attaches to the ends of DNA fragments. The TUNEL assay results confirmed marked apoptosis in pancreatic cells.

The ability to induce apoptosis of cancer cells is an attractive feature of anticancer agents (Houghton, Curr Opin Oncol 1999;11:475–481). Because the caspase cascade plays an important role in the apoptotic program of cells (Thornberry et al., Science 1998; 281: 1312–1316; Mancini et al., J Cell Biol 1998; 140: 1485–1495; Kothakota et al., Science 1997; 278: 294–298), caspases 3, 7 and 9 were analyzed by western blotting. All three caspases were activated by frondoside A. Sequence alignment of caspases 3, 7, and 9 reveals the structural basis of their functions. The executioner caspases 3 and 7 share 54% sequence homology and the backbone structures are nearly identical (Chai et al., Cell 2001; 104: 769–780). These effector caspases are activated by the initiator, caspase 9 through proteolytic cleavage at specific internal Asp residues. In turn, caspase 3 and 7 are responsible for initiating the apoptotic program (Thornberry et al., supra; Mancini et al., supra; Kothakota et al., supra). The Bcl-2 protein family are broadly classified into two categories, according to their role in apoptosis, as anti-apoptotic members such as Bcl-2, Mcl-1, and Bcl-xl and pro-apoptotic members such as Bax, Bad, Bak, and Bag.

These proteins indirectly regulate the activation of the caspase cascade (Boucher et al., J. Cell. Biochem. 2000; 79:355–369; Harris and Thompson, Cell Death Differ., 2000; 7:1182–1191). It is believed that the ratio of anti-apoptotic proteins and pro-apoptotic proteins, which can form homodimers or interact with each other to form heterodimers, determines whether or not cells will undergo apoptosis (Boucher et al., supra; Harris et al., supra). The increase of Bax and the decrease of Bcl-2 and Mcl-1 concentrations indicate that the balance has changed in favor of apoptosis. Taken together, the results indicate that the mitochondrial pathway to caspase cascade activation plays an important role in frondoside A-induced apoptosis.

The ability to induce apoptosis in cancer cells, without affecting healthy cells, as well as minimizing side-effects are major goals for the development of new anticancer agents. Experiments conducted during the course of development of the present invention indicate that frondoside A inhibits cell proliferation, coincident with an increase in p21 expression and induces apoptosis on pancreatic cancer cell via the mitochondrial pathway of caspase cascade activation. Low concentrations of frondoside A caused a marked decrease in tumor growth in a mouse xenograft model using a highly malignant poorly-differentiated human pancreatic cancer cell line. These findings indicate the frondoside A has potent anti-proliferative effects on human pancreatic cancer cell with induction of apoptosis.

I. Frondoside Compositions

Accordingly, in some embodiments, the present invention provides methods and compositions for the treatment of cancer and other angiogenic diseases using Frondosides (e.g., Frondoside A or B). Frondosides are saponins derived from sea cucumber. Examples include Frondoside A, Frondoside B (Findlay et al., J Nat. Prod. 55:93 [1992]), Frondoside C (Avilov et al., Can J. Chem./Rev. Can. Chim. 76:137 [1998]) and Frondoside D (Yayli et al. Phytochemistry 50:135 [1999]).

Frondoside A from sea cucumber has the chemical structure: 3-O-methyl-β-D-glucopyranosyl-(1→3)-β-D-xylopyranosyl-(1→4)-[β-D-xylopyranosyl-(1→2)]-β-D-quinovopyranosyl-(1→2)-4-O-sodium sulfate-β-D-xylopyranosyl-3-O-holost-7(8)-en-3β-ol-16β-O-acetate. The present invention is not limited to the specific chemical structure described above. Variants with similar or enhanced activity, as well as additional frondoside compounds (e.g., frondoside B from sea cucumber) find use in the present invention. Frondoside B has the structure: 3 beta-O-{3-O-methyl-beta-D-glucopyranosyl-(1→3)-O-beta-D-6-sulfonatoglucopyranosyl-(1→4)-O-[beta-D-xylopyranosyl-(1→2)]-O-beta-D-quinovopyranosyl-(1→2)-O-beta-D-4-sulfonatoxylopyranosyl}-holost-7-ene sodium (or potassium) salt.

Frondosides (e.g. frondosides A and B) are tested for their anti-cell proliferation and anti-angiogenesis activities using any suitable assay including, but not limited to, those disclosed in the experimental section below. Preferred frondosides for use in the methods and compositions of the present invention are those that exhibit anti-cancer and anti-cell proliferation and anti-angiogenesis activity.

II. Pharmaceutical Compositions

The present invention further provides pharmaceutical compositions (e.g., comprising the frondoside compounds described above. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which compositions of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24, 25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether.

In some embodiments, drug delivery systems are used that deliver the pharmaceutical compositions of the present invention directly to the gut. Several types of colonic drug delivery systems are currently available, including enemas (Sutherland et al., Med. Clin. North Amer., 74, 119 (1990)); rectal foams (Drug. Ther. Bull., 29, 66 (1991)); and delayed release oral formulations in the form of Eudragit-coated capsules which dissolve at pH 7 in the terminal ileum (Schroeder et al., New Engl. J. Med., 317, 1625 (1987)). In other embodiments enteric coatings, which remain undissociated in the low pH environment of the stomach, but readily ionize when the pH rises to about 4 or 5 are utilized, including, but not limited to, polyacids having a pH of 3 to 5.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual compositions of the present invention, and the delivery means, and can generally be estimated based on $EC_{50}$s found to be effective in in vitro and in vivo animal models or based on the examples described herein. In general, dosage is from 0.01 μg to 10 mg per kg of body weight, and may be given once or more daily, weekly, monthly or yearly. In some embodiments, dosage is continuous (e.g., intravenously) for a period of from several hours to several days or weeks. In some embodiments, treatment is given continuously for a defined period followed by a treatment free period. In some embodiments, the pattern of continuous dosing followed by a treatment free period is repeated several times (e.g., until the disease state is diminished).

The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the composition is administered in maintenance doses, ranging from 0.01 μg to 10 mg, preferably from 0.1 μg to 1000 μg, and even more preferably from 0.1 μg to 100 μg per kg of body weight, orice or more daily, to once every 20 years.

II. Combination Therapy

In some embodiments, the frondoside compositions of the present invention are provided in combination with existing therapies. In some embodiments, the frondoside compounds of the present invention are provided in combination with known cancer chemotherapy agents. The present invention is not limited to a particular chemotherapy agent.

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. The below Table provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin A$_2$ and bleomycin B$_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |

-continued

| | | |
|---|---|---|
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by Streptomyces parvullus, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S, 3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-,3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |

-continued

| | | |
|---|---|---|
| Etoposide phosphate (4'-Demethylepipodophyllotoxin 9-[4,6-O-(R)-ethylidene-(beta)-D-glucopyranoside],4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$ ·$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4': 6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S.HCl$) | Ergamisol | Janssen Research Foundation, Titusville, NJ |
| Lomustine | CeeNU | Bristol-Myers Squibb |

| | | |
|---|---|---|
| (1-(2-chloro-ethyl)-3-cyclohexyl-1-nitrosourea) | | |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β, 20-Epoxy-1,2a, 4, 7β, 10β, 13a-hexaahydroxytax-11-en-9-one 4,10-diacetate 2-benzoate 13-ester with (2R, 3 S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11–17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |

-continued

| | | |
|---|---|---|
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}$ $(OH)_2$) | Sclerosol | Bryan, Corp., Woburn, MA |
| Tamoxifen ((Z)2-[4-(1,2-diphenyl-1-butenyl) phenoxy]-N, N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| Teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10}\cdot H_2SO_4$) | Velban | Eli Lilly |
| Vincristine ($C_{46}H_{56}N_4O_{10}\cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

III. Treatment of Angiogenic Diseases

As described above, the Frondoside A and B compositions of the present invention have been shown to have apoptotic promoting activity in cancer cells. Accordingly, as described above, the compositions and methods find use in the treatment of cancer. The present invention is not limited to the treatment of a particular cancer. Exemplary cancers that are suitable for treatment with the methods and compositions of the present invention include prostate, breast, pancreatic, skin, leukemia, head and neck tumors, Kaposi's sarcoma, and bladder cancer.

The present invention is further not limited to the treatment of cancer. The present invention is not limited to a particular mechanism. Indeed, an understanding of the mechanism is not necessary to practice the present invention. Nonetheless, it is contemplated that, based on the apoptotic promoting activities of Frondoside A and B, that the compounds find use in the treatment of other diseases characterized by aberrant angiogenesis.

Accordingly, in some embodiments, the present invention also provides methods for treating neovascular diseases of the eye, including for example, corneal neovascularization, neovascular glaucoma, proliferative diabetic retinopathy, retrolental fibroplasia and macular degeneration. The present invention further provides compositions and methods for the treatment of other diseases characterized by aberrant angiogenesis including, but not limited to fibrotic diseases (e.g., chronic pulmonary fibrosis).

Briefly, corneal neovascularization as a result of injury to the anterior segment is a significant cause of decreased visual acuity and blindness, and a major risk factor for rejection of corneal allografts. As described by Burger et al., Lab, Invest. 48:169–180, 1983, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

Currently no clinically satisfactory therapy exists for inhibition of corneal neovascularization or regression of existing corneal new vessels. Topical corticosteroids appear to have some clinical utility, presumably by limiting stromal inflammation.

Thus, within one aspect of the present invention methods are provided for treating neovascular diseases of the eye such as corneal neovascularization (including corneal graft neovascularization), comprising the step of administering to a patient a therapeutically effective amount of an anti-angiogenic composition (e.g., Frondoside A or B) to the cornea, such that the formation of blood vessels is inhibited.

Within particularly preferred embodiments of the invention, an anti-angiogenic factor (e.g., Frondoside A or B) may be prepared for topical administration in saline (combined with any of the preservatives and antimicrobial agents commonly used in ocular preparations), and administered in eyedrop form. The Frondoside A or B solution or suspension may be prepared in its pure form and administered several times daily. Alternatively, Frondoside A or B may also be administered directly to the cornea, within preferred embodiments, the e.g., Frondoside A or B composition is prepared with a muco-adhesive polymer which binds to cornea. Within further embodiments, the Frondoside A or B compositions may be utilized as an adjunct to conventional steroid therapy.

Topical therapy may also be useful prophylactically in corneal lesions that are known to have a high probability of inducing an angiogenic response (such as chemical burns). In these instances the treatment, likely in combination with steroids, may be instituted immediately to help prevent subsequent complications.

Within other embodiments, the Frondoside A or B compositions described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

In other embodiments, the present invention provides compositions and methods are provided for treating neovascular glaucoma, comprising the step of administering to a patient a therapeutically effective amount of a Frondoside A or B composition to the eye, such that the formation of blood vessels is inhibited.

Briefly, neovascular glaucoma is a pathological condition wherein new capillaries develop in the iris of the eye. The angiogenesis usually originates from vessels located at the pupillary margin, and progresses across the root of the iris and into the trabecular meshwork. Fibroblasts and other connective tissue elements are associated with the capillary growth and a fibrovascular membrane develops which spreads across the anterior surface of the iris. Eventually this tissue reaches the anterior chamber angle where it forms synechiae. These synechiae in turn coalesce, scar, and contract to ultimately close off the anterior chamber angle. The scar formation prevents adequate drainage of aqueous humor through the angle and into the trabecular meshwork, resulting in an increase in intraocular pressure that may result in blindness.

Neovascular glaucoma generally occurs as a complication of diseases in which retinal ischemia is predominant. In particular, about one third of the patients with this disorder have diabetic retinopathy and 28% have central retinal vein occlusion. Other causes include chronic retinal detachment, end-stage glaucoma, carotid artery obstructive disease, retrolental fibroplasia, sickle-cell anemia, intraocular tumors, and carotid cavernous fistulas. In its early stages, neovascular glaucoma may be diagnosed by high magnification slitlamp biomicroscopy, where it reveals small, dilated, disorganized capillaries (which leak fluorescein) on the surface of the iris. Later gonioscopy demonstrates progressive obliteration of the anterior chamber angle by fibrovascular bands. While the anterior chamber angle is still open, conservative therapies may be of assistance. However, once the angle closes surgical intervention is required in order to alleviate the pressure.

In some embodiments, Frondoside A or B is administered topically to the eye in order to treat early forms of neovascular glaucoma. In other embodiments of the invention, Frondoside A or B compositions are implanted by injection of the composition into the region of the anterior chamber angle. This provides a sustained localized increase of anti-angiogenic factor, and prevents blood vessel growth into the area. Implanted or injected anti-angiogenic compositions which are placed between the advancing capillaries of the iris and the anterior chamber angle can "defend" the open angle from neovascularization. As capillaries will not grow within a significant radius of the anti-angiogenic composition, patency of the angle could be maintained. Within other embodiments, the anti-angiogenic composition may also be placed in any location such that the anti-angiogenic factor is continuously released into the aqueous humor. This would increase the anti-angiogenic factor concentration within the humor, which in turn bathes the surface of the iris and its abnormal capillaries, thereby providing another mechanism by which to deliver the medication. These therapeutic modalities may also be useful prophylactically and in combination with existing treatments.

In still further embodiments, the present invention provides methods for treating proliferative diabetic retinopathy. In yet other embodiments, the present invention provides compositions and methods for treating retrolental fibroplasia.

In addition to cancer, however, numerous other non-tumorigenic angiogenesis-dependent diseases which are characterized by the abnormal growth of blood vessels may also be treated with the Frondoside A or B compositions of the present invention. Representative examples of such non-tumorigenic angiogenesis-dependent diseases include hypertrophic scars and keloids, proliferative diabetic retinopathy, rheumatoid arthritis, arteriovenous malformations, atherosclerotic plaques, delayed wound healing, hemophilic joints, nonunion fractures, Osier-Weber syndrome, psoriasis, pyogenic granuloma, scleroderma, tracoma, menorrhagia, vascular adhesions, proliferative vitreoretinopathy including those forms not associated with diabetes, hemangioma, and retrolental fibroplasias.

EXPERIMENTAL

The following examples are provided in order to demonstrate and further illustrate certain preferred embodiments and aspects of the present invention and are not to be construed as limiting the scope thereof.

Example 1

Frondoside A Anti Pancreatic Cancer Activity

This Example describes the anti pancreatic cancer activity of Frondoside A.

A. Materials and Methods

Frondoside A extraction. *Cucumaria frondosa* was fished from the seabed near Stonington, Me., size reduced and freeze-dried commercially. One kilogram of freeze-dried *C. frondosa* (from 19 kg live) was extracted by supercritical $CO_2$ at 5500 psi at 60° C. over 4 hours to remove non-polar lipids. The non-lipid residue fraction was then extracted repeatedly (1:10) with ethanol/water (70:30) at room temperature. The aqueous extract was evaporated to dryness (879 mg) and passed through an Amberlite-XAD-2 column and eluted with 10 volumes distilled water until it was shown to be salt free ($AgNO_3$ test), followed by methanol (5 volumes). The methanol eluate was evaporated under reduced pressure to give 304 milligrams of crude glycoside material. This dry glycoside material was subjected to chromatography on Davisil C-18 reversed phase (35–75:m) using water, then a water-methanol gradient and finally methanol as eluents. Fractions eluted with 70% and 80% methanol contained Frondosides A, B and C and some other unidentified saponins (143 mg) (as compared with pure Frondoside A standards on TLC). These fractions were combined and subjected to column chromatography on $SiO_2$ gel, eluted with $CH_3Cl_2$-methanol-$H_2O$, acetone and methanol. Fractions eluted with $CH_3Cl_2$-methanol-$H_2O$ (5:5:1) (lower phase) and acetone were combined and submitted to repeated reversed-phase HPLC (octadecyl silica eluted with methanol-$H_2O$ 50%) to give pure Frondosides A (102 mg) and B (56 mg) after combining the target eluates.

Smaller versions of this method were altered to include supercritical $CO_2$ with co-solvents of ethanol/water (70:30) to obtain crude aqueous extract, which was then subjected to Amberlite XAD-2 chromatography. This former method seems to simplify the remaining steps in obtaining the pure Frondoside A inasmuch as there are decreased levels of di-and tri-sulfated glycosides remaining in the aqueous product prior to XAD-2 de-salting.

Additional studies were performed with crude *C. frondosa* cook-water (CW) that was shown to be a 0.05% glycoside containing product.

Reagents. Frondoside A was diluted to the appropriate concentrations in serum-free medium for the experiments. The enhanced chemiluminescence system (ECL) was obtained from Santa Cruz Biotechnology, Inc (Santa Cruz, Calif.). The mouse monoclonal antibodies against Bax, Bcl-2, Mcl-1, P21 and P27 and the rabbit polyclonal antibodies against caspase 3, caspase 7, and caspase 9 were purchased from Santa Cruz Biotechnology, Inc. (Santa Cruz, Calif.). Unless otherwise stated, all other chemicals were purchased from Sigma (St Louis, Mo., USA).

Cell culture. The poorly differentiated human pancreatic cancer line AsPC-1 was purchased from the American Type Culture Collection (ATCC, Manassas, Va., USA). Cells were cultured in MEM medium supplemented with penicillin G (100 U/mL), streptomycin (100 U/mL) and 10% FBS at 37° C. in humidified air with 5% CO2. Cells were harvested by incubation in trypsin-EDTA solution for 10–15 minutes. Cells were then centrifuged at 300×g for 5 minutes and cell pellets were suspended in fresh culture medium prior to seeding into culture flasks or plates.

Morphological studies. The photomicrographs of cell morphological changes were taken with a Kodak DC 120 digital zoom camera under an inverted microscope (400×) following treatment with or without 4 μg/mL frondoside A for different time periods from 24 to 72 hours.

Cell proliferation assay. Cell growth was analyzed by $^3$H-methyl thymidine incorporation and cell counting. Following treatment of pancreatic cancer cells with a series of concentrations of frondoside A from 1 μg/mL to 16 μg/mL, cellular DNA synthesis was assayed by adding $^3$H-methyl thymidine at 0.5 μLCi/well. After 2 hours incubation, the cells were washed twice with PBS, precipitated with 10% TCA for two hours, and solubilized from each well with 0.5 ml of 0.4 N NaOH. Incorporation of $^3$H-methyl thymidine into DNA was measured by adding scintillation liquid and counting in a scintillation counter (LKB BackBeta, Wallac, Turku, Finland). For cell counting, cells were seeded in 12 wells plates and cultured with serum-free medium for 24 hours prior to frondoside A treatment and then switched to serum-free medium with or without 4 µg/mL frondoside A for the respective treatment time points (24, 48 and 72 hours). The cells were removed from the plate by trypsinization to produce a single cell suspension for cell counting. The cells were counted using Z1-Coulter Counter (Luton, UK).

Annexin V assay. Cells grown on coverslips were treated with or without 4 µg/mL frondoside A for 4 hours. The cells were then rinsed with PBS and 500 µL of assay buffer once. Then, 200 µL of assay buffer, 4 µL of annexin-V FITC, and 20 µL of propidium iodide were added to each coverslip. The coverslip were then incubated at room temperature for 15 min in the dark and washed once with PBS. Cells were finally viewed under fluorescence microscope using a dual filter set for FITC and rhodamine, and pictures were taken using a Kodak DC 120 digital zoom camera (Eastman Kodak Company, Rochester, N.Y.).

Terminal deoxynucleotidyl transferase-mediated deoxyuridine triphosphate nick-end labeling (TUNEL) assay. The assay was carried out for terminal incorporation of fluorescein 12-dUTP by terminal deoxynucleotidyl transferase into fragmented DNA in cancer cells (TUNEL assay kits, Promega, Madison, Wis.). Cells were cultured to 50%–60% confluence in T75 flasks in serum-free conditions for 24 hours and then treated with or without 4 µg/mL Frondoside A for 72 hours. Cells were then trypsinized and fixed in 1% methanol-free formaldehyde-PBS for 15 minutes. At the end of treatment, cells were harvested with trypsin-EDTA solution to produce a single cell suspension. Cells were then pelleted by centrifugation and washed twice with PBS. Cell pellets were suspended in 0.5 ml PBS and fixed in ice-cold 70% ethanol at 4° C. Fixed cells were centrifuged at 300×g for 10 minutes and pellets were washed with PBS. After resuspension with 1 ml PBS, cells were incubated with 10 µL of RNase I (10 mg/mL) and 100 µL of propidium iodide (400 µg/mL; Sigma) and shaken for 1 hour at 37° C. in the dark. Samples were analyzed by flow cytometry. Laser flow cytometry was used to quantify the green fluorescence of fluorescein-12-dUTP incorporated against the red fluorescence of propidium iodide.

Western blotting. Cells were seeded into flasks and cultured to 50% to 60% confluence for 24 hours. Cells were then placed in serum-free medium with or without 4 µg/mL frondoside A for periods of 0, 24, 48 and 72 hours respectively. Proteins were extracted from attached and floating cells in lysis buffer containing 4% SDS. Protein concentrations were determined using the bicinchoninic acid assay with BSA as standard. Western blotting was carried out. In brief, equal amounts of protein in the cell lysates were separated on 15% SDS-PAGE and the proteins were transferred onto nitrocellulose membranes. After blocking non-specific sites with dried milk, membranes were incubated with the appropriate dilution of primary antibody. Membranes were then incubated with a horseradish peroxidase conjugated secondary antibody. Proteins were detected using an enhanced chemiluminescence detection system.

Animal Study. Athymic mice (BALB/c nu/nu, 5-week old females) were purchased from Charles River Laboratories (Wilmington, Mass.). Mice were acclimatized to the animal facility for one week prior to receiving xenografts. Xenografts of three million AsPC-1 cells were injected into the flanks of mice. Once visible tumors were evidenced 4–5 days after injection, the animals were divided equally into two groups (6 animals/group) and treated with frondoside A (10 µg/kg/day) or control vehicle (100 µL phosphate-buffered saline, PBS) by intraperitoneal injection. Animal weight and tumor size were recorded every three days. The formula used for tumor volume was (length)H(width)H(length+width/2)H0.526=volume (Naito et al., Int. J. Cancer 58:730 [1994]). After 4-weeks of treatment the animals were euthanized and the tumors were carefully dissected and tumor weights measured.

Statistical analysis. Data was analyzed by analysis of variance (ANOVA) with Bonferonni's or Dunnet's multiple comparison post-tests, as appropriate, for significance between individual groups. This analysis was performed with the Prism software package (GraphPad, San Giego, Calif.). Data are expressed as mean±SEM. Data represent of at least 3 different experiments.

B. Results

Effect of frondoside A on thymidine incorporation in pancreatic cancer cells. Frondoside A caused marked inhibition of thymidine incorporation in AsPC-1 cells in a concentration-dependent manner at concentrations ranging from 1 µg/mL to 16 µg/mL (FIG. 1). Cytotoxicity was only seen following treatment with frondoside A concentrations higher than 16 µg/mL, which caused cell necrosis.

Figure 2:
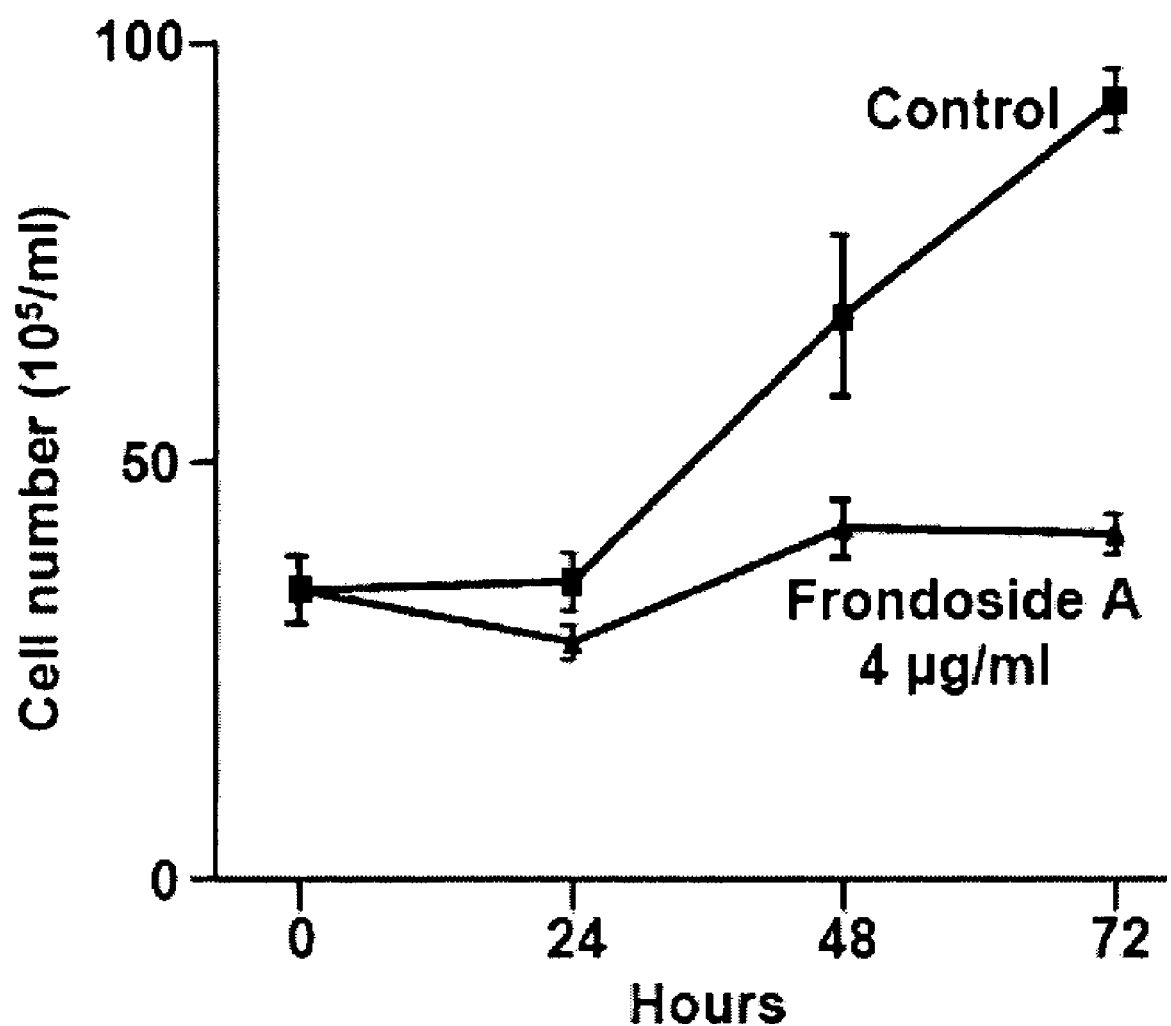
FIG. 2 shows a time-course effect of 4 μg/mL frondoside A on cell number in AsPC-1 cells. Data represent means±SEM of three separate experiments. *=$P<0.05$, =$P<0.01$, *=$P<0.001$ compared to control.

Effect of frondoside A on pancreatic cancer cell proliferation measured by cell counting. Frondoside A significantly inhibited proliferation of pancreatic cancer cells in a time-dependent manner, as measured by cell number in AsPC-1 cells (FIG. 2). During the first 24 hours, no obviously effect was seen compared to control. At 48 and 72 hours, frondoside A resulted in a marked and progressive decrease in cell number compared to control.

Apoptosis of pancreatic cancer cells induced by frondoside A. Within 24 hours 4 µg/mL frondoside A caused the marked morphological changes characteristic of apoptosis, including shrinkage of cytoplasm, membrane blebbing, nuclear condensation, and loss of adhesion. To further characterize the apoptosis observed, the early apoptotic changes in the cellular membrane were investigated by annexin V binding assay and late changes by analysis of DNA fragmentation was carried out using the TUNEL assay. Annexin V binding was observed in response to 4 µg/mL frondoside A treatment within 3 hours. TUNEL staining of pancreatic cancer cells was markedly increased by 4 µg/mL frondoside A treatment at 72 hours (control 2.4%, frondoside A 36.1%, P<0.001).

Figure 3:
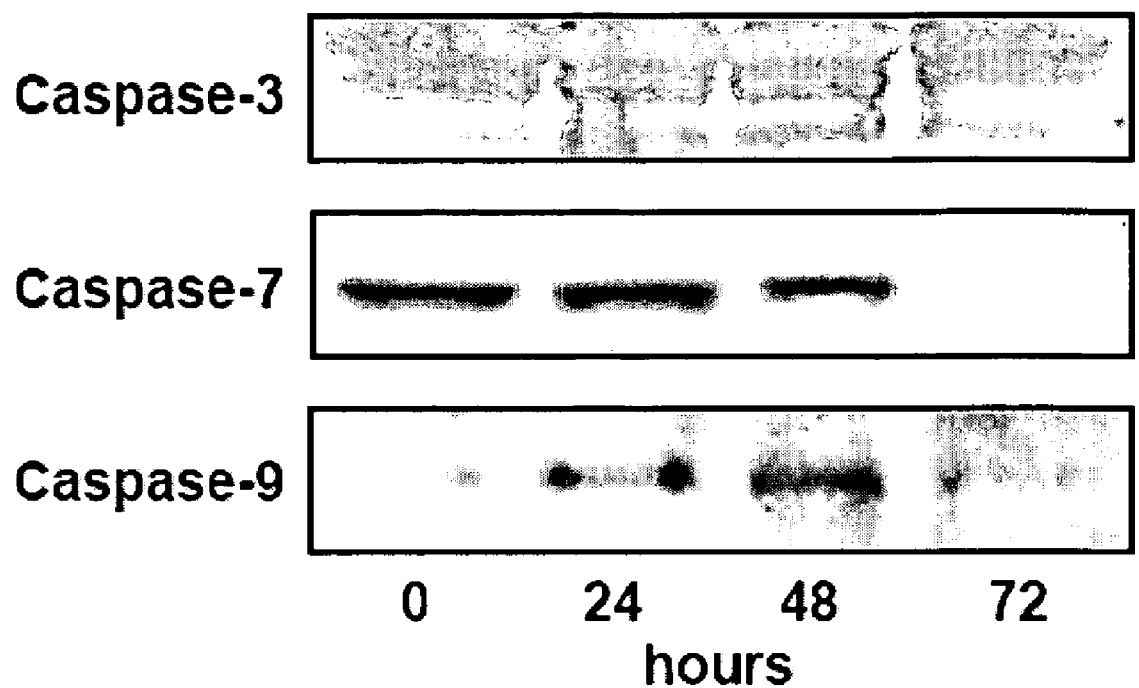
FIG. 3 shows Western blotting showing the effect of 4 μg/mL frondoside A on caspases 3, 7, 9 in AsPC-1 cells.

Effect of frondoside A on activation of caspase 3, 7, and 9 proteins. The expression and activation of caspases 3, 7 and 9 by cleavage were observed by western blotting. In response to frondoside A, the procaspase 3 was cleaved into products of lower molecular weight, including a band corresponding to the 85 kDa active form (FIG. 3). Only the uncleaved 116 kDa procaspase-3 was seen in untreated controls. Activation of caspases 7 and 9 were documented by a reduction in the amounts of the respective procaspase forms, as the antibodies do not recognize the active fragments (FIG. 3). Activation of caspases 3, 7 and 9 were induced in a time-dependent manner, coincident with the induction of apoptosis.

Figure 4:
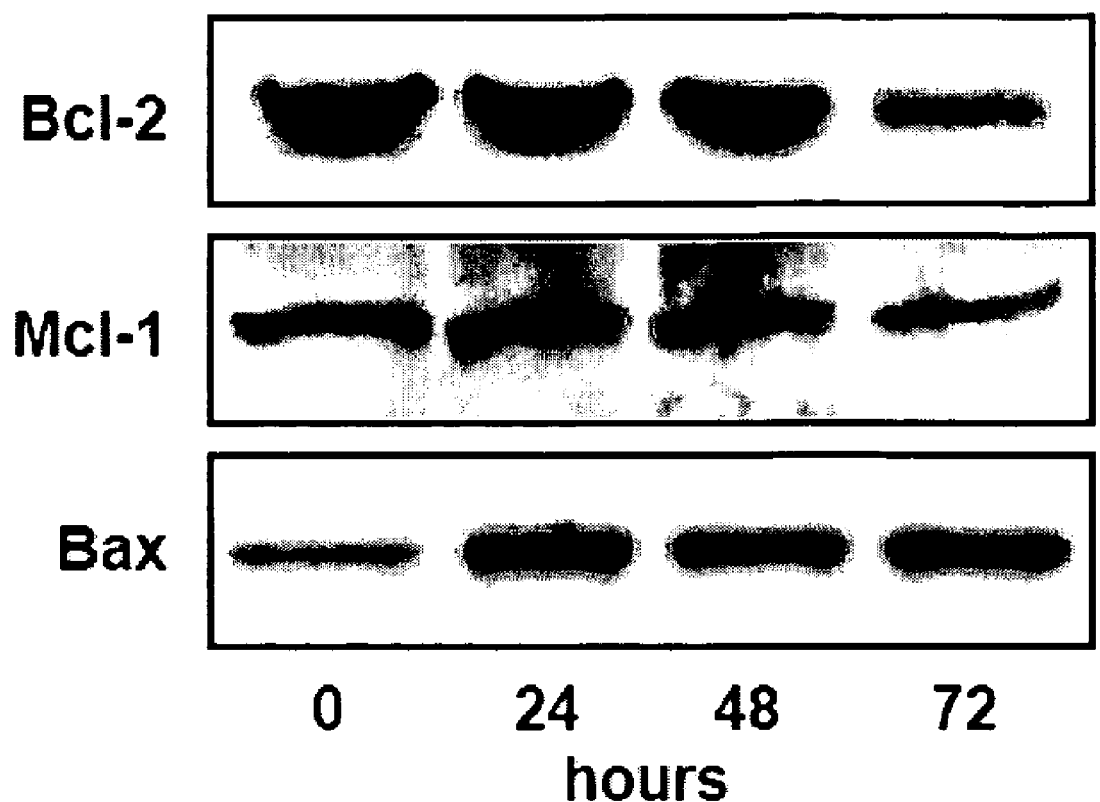
FIG. 4 shows Western blot showing the effect of 4 μg/mL frondoside A on the Bcl-2, Mcl-1, and Bax proteins in AsPC-1 cells. The results are representative of three separate experiments.

Effect of frondoside A on expression of Bax, Bcl-2, and Mcl-1 proteins. Treatment with frondoside A decreased expression of the anti-apoptotic proteins, Bcl-2 and Mcl-1 in a time-dependent manner (FIG. 4). In contrast, concentrations of the pro-apoptotic protein Bax increased (FIG. 4).

Figure 5:
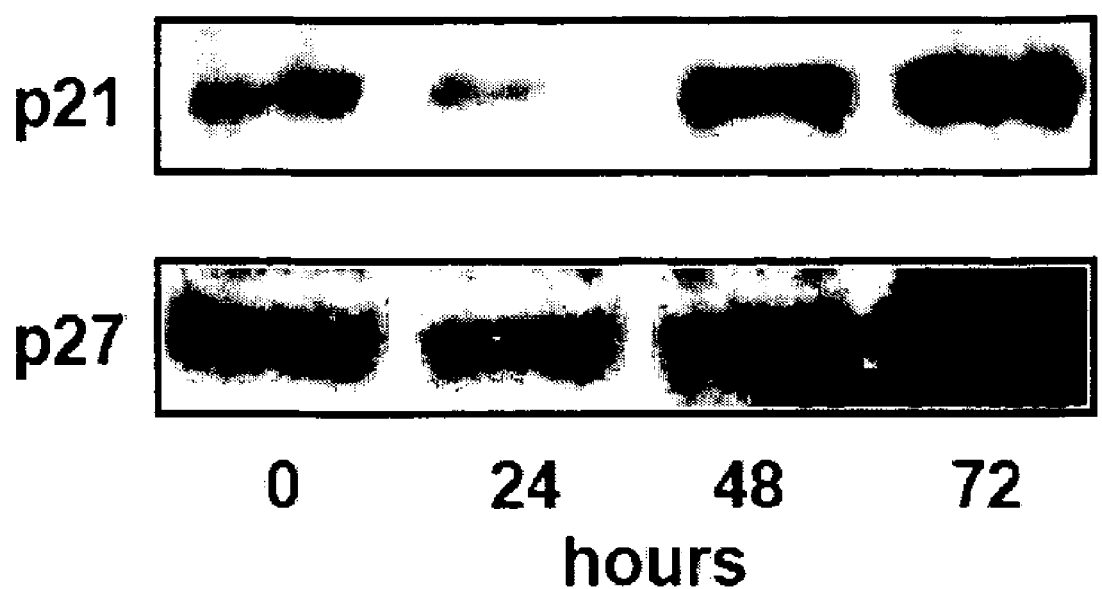
FIG. 5 shows Western blot showing the effect of 4 μg/mL frondoside A on the cyclin-dependent kinase inhibitors, p21 and p27 in AsPC-1 cells. The results are representative of three separate experiments.

Effect of frondoside A on expression of P21 and P27. In response to frondoside A, expression of the cyclin-dependent kinase inhibitor, P21$^{Waf1}$ was markedly increased in a time-dependent manner, while expression of p27$^{Kip1}$ was not changed (FIG. 5).

Figure 6:
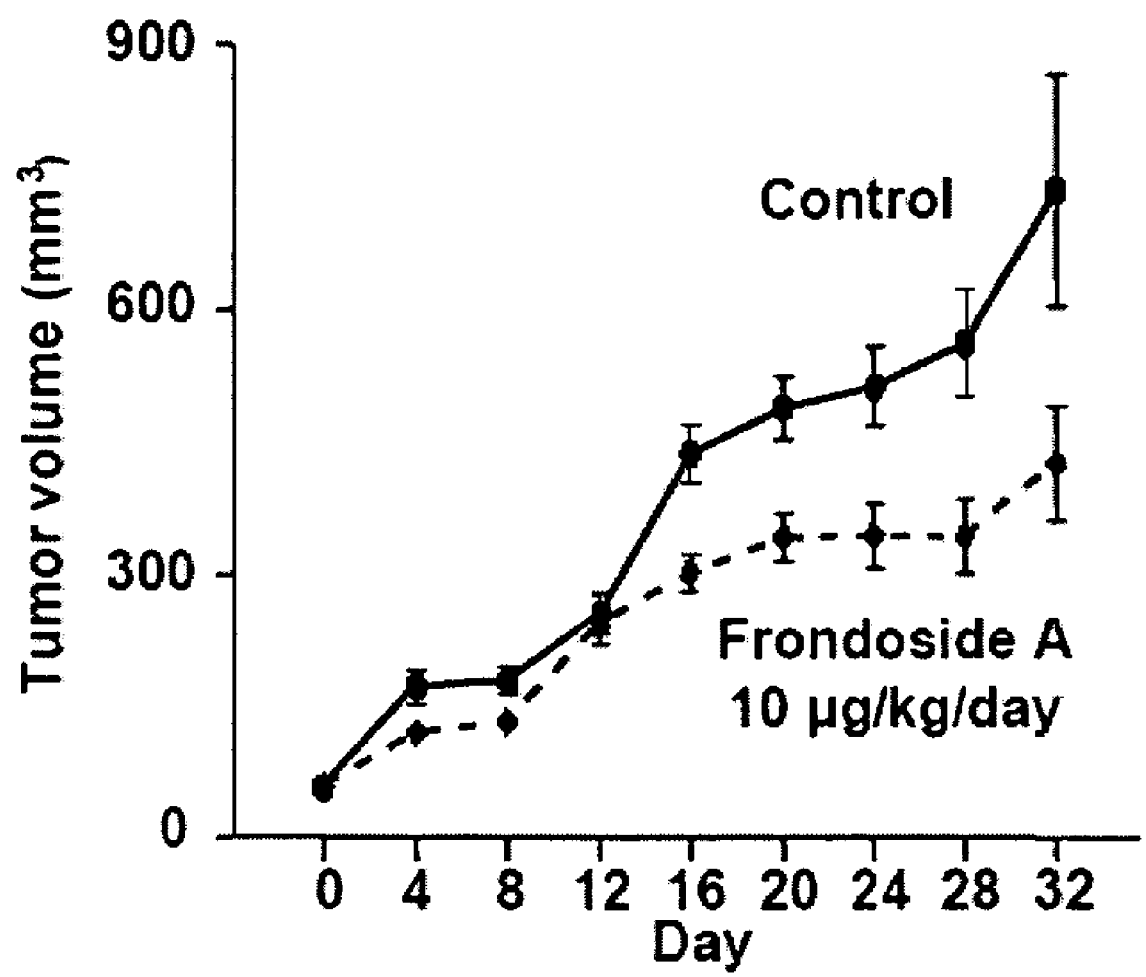
FIG. 6 shows the effect of frondoside A (10 μg/kg/day) on growth of AsPC-1 human pancreatic cancer xenografts in athymic mice.

Effect of frondoside A on pancreatic cancer growth and in vivo. The growth inhibitory effect of frondoside A was confirmed in an in vivo study. Frondoside A at 10 μg/kg/day markedly inhibited the growth of subcutaneously transplanted AsPC-1 cells in athymic mice after 4-weeks of treatment, as measured by both tumor volume and tumor weight (FIG. 6). No toxicity was seen with frondoside A through the treatment period, and there was no significant difference between the body weights of control and treated animals.

Example 2

Inhibition of Colon Cancer Cell Growth

This Example describes the inhibition of proliferation of colon cancer cells by Frondoside A.

A. Methods

Test Substance and Concentration. Frondoside A (CBR-24) was dissolved in 100% DMSO and then diluted with sterile distilled water to obtain initial working solutions of 10000, 1000, 100, 10, and 1 μM in 40% DMSO. A 100-fold dilution was further made in culture media to generate final assay concentration of 100, 10, 1, 0.1 and 0.01 μM in 0.4% of DMSO.

Cell Line and Culture Media. The tumor cell line DLD-1 (human colon adenocarcinoma), obtained from American Type Culture Collection (ATCC CCL-221), was incubated in 95% air-5% $CO_2$ gas mixture at 37° C. The culture medium used was RPMI 1640 with 10% fetal bovine serum, which was supplemented with 1% Antibiotic-Antimycotic.

Chemicals. AlamarBlue (Biosource, USA), Antibiotic-Antimycotic (GIBCO BRL, USA), Dimethylsulfoxide (Merck, Germany), Fetal Bovine Serum (HyClone, USA), Mitomycin (Kyowa, Japan), and RPMI 1640 (HyClone, USA).

Equipment. $CO_2$ Incubator (Form a Scientific Inc., USA), Centrifuge 5810R (Eppendorf, Germany), Hemacytometer (Hausser Scientific Horsham, USA), Inverted Microscope CK-40 (Olympus, Japan), System Microscope E-400 (Nikon, Japan), Spectrafluor Plus (Tecan, Austria) and Vertical Laminar Flow (Tsao Hsin, R. O. C.).

Evaluation of anti-proliferation for test substances. Aliquots of 100 μl of cell suspension (about 2.5×10$^3$ cells/well) were placed in 96-well microtiter plates in an atmosphere of 5% $CO_2$ at 37° C. After 24 hours, 100 μl of growth medium and 2 μL of test solution, mitomycin or vehicle (40% DMSO), were added per well, in duplicate, for an additional 72-hour incubation. Thus, the final concentration of DMSO was 0.4%. The Frondoside A was evaluated for possible inhibitory effects on cell proliferation at concentrations of 100, 10, 1, 0.1 and 0.01 μM. At the end of incubation, 20 μl of 90% alamarBlue reagent was added to each well for another 6 hour incubation before detection of cell viability by fluorescent intensity. Fluorescent intensity was measured using a Spectrafluor Plus plate reader with excitation at 530 nm and emission at 590 nm.

Determination of IC50, TGI and LC50. The measured results were calculated by the following formula:

$$PG(\%)=100\%\times(\text{Mean } F_{test}-\text{Mean } F_{time0})/(\text{Mean } F_{ctrl}-\text{Mean } F_{time0})$$

$$\text{If (Mean } F_{test}-\text{Mean } F_{time0})<0, \text{ then } PG\ (\%)=100\%\times(\text{Mean } F_{test}-\text{Mean } F_{time0})/(\text{Mean } F_{time0}-\text{Mean } F_{blank})$$

Where:

PG: percent growth

Mean $F_{time0}$=The average of 2 measured fluorescent intensities of reduced alamarBlue at the time just before exposure of cells to the test substance.

Mean $F_{test}$=The average of 2 measured fluorescent intensities of alamarBlue after 72-hour exposure of cells to the test substance.

Mean $F_{ctrl}$=The average of 2 measured fluorescent intensities of alamarBlue after 72-hour incubation without the test substance.

Mean $F_{blank}$=The average of 2 measured fluorescent intensities of alamarBlue in medium without cells after 72-hour incubation.

A decrease of 50% or more ($\geq$50%) in fluorescent intensity relative to vehicle-treated control indicated significant cell growth inhibition, cytostatic or cytotoxic activity, and semi-quantitative $IC_{50}$, TGI and $LC_{50}$ were then determined by nonlinear regression using GraphPad Prism (GraphPad Software, USA).

IC50 (50% Inhibition Concentration): Test compound concentration where the increase from time$_0$ in the number or mass of treated cells was only 50% as much as the corresponding increase in the vehicle control at the end of experiment.

TGI (Total Growth Inhibition): Test compound concentration where the number or mass of treated cells at the end of experiment was equal to that at time$_0$.

LC50 (50% Lethal Concentration): Test compound concentration where the number or mass of treated cells at the end of experiment was half that at time$_0$.

B. Results

Figure 7:
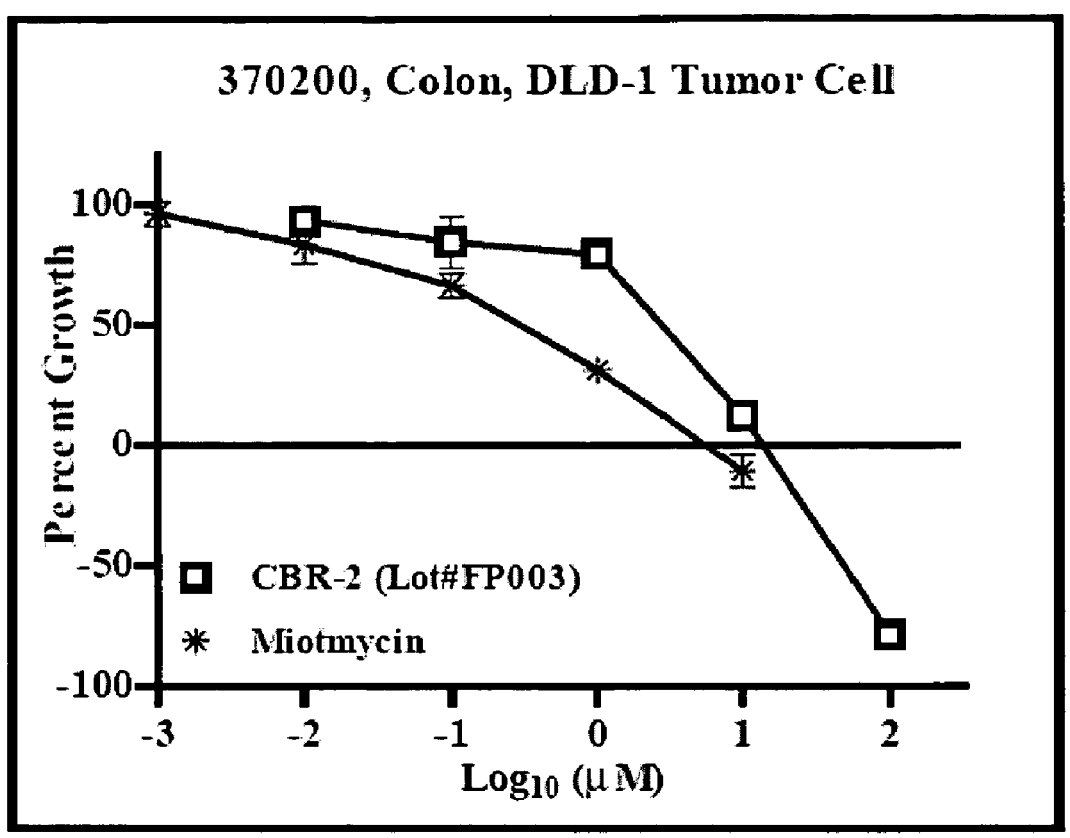
FIG. 7 shows the effect of frondoside A on growth of colon cancer cells.

The results are shown in FIG. 7 and Tables 1 and 2. Frondoside A at doses of 10 μM and 100 μM caused significant growth inhibition of DLD-1 cells ($\leq$50% of cell proliferation) relative to the vehicle-treated control. Significant activity was observed for the concurrently-tested positive control Mitomycin, at <10 μM (Table 1 and FIG. 7). Semiquantitative determinations of estimated $IC_{50}$ (50% inhibition concentration), TGI (total growth inhibition) and LC50 (50% lethal concentration) values were calculated by nonlinear regression analysis and the results are shown on Table 2 below:

TABLE 1

Effects of Test Substances on the Growth of DLD-1 Tumor Cell

| | | | | | Percent Growth (Mean ± SEM, n = 2) | | | | |
|---|---|---|---|---|---|---|---|---|---|
| | | | | | Concentration (μM) | | | | |
| Treatment | Assay Name | Blank | $Time_0$ | Vehicle | 100 | 10 | 1 | 0.1 | 0.01 |
| PT# 1045143 (CBR-24) [CBR-2 (Lot # FP003)] | 370200, Colon, DLD-1 | −100 | 0 | 100 | −79 ± 5 | 12 ± 0 | 79 ± 5 | 84 ± 11 | 93 ± 5 |
| | | | | | Concentration (μM) | | | | |
| | | | | | 10 | 1 | 0.1 | 0.01 | 0.001 |
| Mitomycin | 370200, Colon, DLD-1 | −100 | 0 | 100 | −11 ± 7 | 31 ± 4 | 66 ± 5 | 83 ± 8 | 96 ± 5 |

Blank: In duplicate, averaged fluorescent intensity of almarBlue in medium without cells after 3-day incubation period relative to $Time_0$ (transformed and recorded as −100%).
$Time_0$: In duplicate, averaged fluorescent intensity of almarBlue in medium just before exposure of cells to test substance (transformed and recorded as 0%).
Vehicle: In duplicate, averaged fluorescent intensity of almarBlue in medium containing cells and added vehicle after 3-day incubation period relative to $Time_0$ (transformed and recorded as 100%).

A decrease of 50% or more (≧50%) in fluorescent intensity relative to vehicle-treated control indicates significant growth inhibition, cytostatic or cytotoxic activity.

TABLE 2

The Summary of $IC_{50}$, TGI and $LC_{50}$ Values

| Treatment | Assay # | Assay Name | $^aIC_{50}$ | $^bTGI$ | $^cLC_{50}$ |
|---|---|---|---|---|---|
| PT# 1045143 (CBR-24) [CBR-2 (Lot # FP003)] | 370200 | Tumor, colon, DLD-1 | 3.6 μM | 12 μM | 41 μM |
| Mitomycin | 370200 | Tumor, colon, DLD-1 | 0.33 μM | 5.5 μM | >10 μM |

$^aIC_{50}$ (50% Inhibition Concentration): Test compound concentration where the increase from $time_0$ in the number or mass of treated cells was only 50% as much as the corresponding increase in the vehicle control at the end of experiment.
$^bTGI$ (Total Growth Inhibition): Test compound concentration where the number or mass of treated cells at the end of experiment was equal to that at $time_0$.
$^cLC_{50}$ (50% Lethal Concentration): Test compound concentration where the number or mass of treated cells at the end of experiment was half that at $time_0$.

Example 3

Anti-Prostate Cancer Activity of Frondoside A

This Example describes the inhibition of growth of prostate cancer cells by frondoside A.

A. Methods

Test Substance and Concentration. Frondoside A (FAS) was dissolved in 100% DMSO and then diluted with sterile distilled water to obtain initial working solutions of 1000, 300, 100, 30, and 10 μM in 40% DMSO. A 100-fold dilution was further made in culture media to generate final assay concentration of 10, 3, 1, 0.3 and 0.1 μM in 0.4% DMSO.

Cell Line and Culture Media. The tumor cell line PC-3 (human prostate adenocarcinoma), obtained from American Type Culture Collection (ATCC CRL-1435), was incubated in air atmosphere of 5% CO2 at 37° C. The culture medium used was F-12K Nutrient Mixture (Kaighn's Modification) with 3% fetal bovine serum, which was supplemented with 1% Antibiotic-Antimycotic.

Chemicals. AlamarBlue (Biosource, USA), Antibiotic-Antimycotic (GIBCO BRL, USA), Dimethylsulfoxide (Merck, Germany), Fetal Bovine Serum (HyClone, USA), F-12K Nutrient Mixture (Kaighn's Modification), and Mitomycin (Kyowa, Japan).

Equipment. $CO_2$ Incubator (Form a Scientific Inc., USA), Centrifuge 5810R (Eppendorf, Germany), Hemacytometer (Hausser Scientific Horsham, USA), Inverted Microscope CK-40 (Olympus, Japan), System Microscope E-400 (Nikon, Japan), Spectrafluor Plus (Tecan, Austria) and Vertical Laminar Flow (Tsao Hsin, R. O. C.).

Evaluation of anti-proliferation for test substances. Aliquots of 100 μl of cell suspension (about 2.5×10³ cells/well) were placed in 96-well microtiter plates in an atmosphere of 5% $CO_2$ at 37° C. After 24 hours, 100 μl of growth medium and 2 μl of test solution, mitomycin or vehicle (40% DMSO), were added per well, in duplicate, for an additional 72-hour incubation. Thus, the final concentration of DMSO was 0.4%. The Frondoside A was evaluated for possible inhibitory effects on cell proliferation at concentrations of 10, 3, 1, 0.3 and 0.1 μM. At the end of incubation, 20 μl of 90% alamarBlue reagent was added to each well for another 6-hour incubation before detection of cell viability by fluorescent intensity. Fluorescent intensity was measured using a Spectrafluor Plus plate reader with excitation at 530 nm and emission at 590 nm.

Determination of IC50, TGI and LC50. The measured results was calculated by the following formula:

$$PG(\%) = 100\% \times (\text{Mean } F_{test} - \text{Mean } F_{time0})/(\text{Mean } F_{ctrl} - \text{Mean } F_{time0})$$

If (Mean $F_{test}$ − Mean $F_{time0}$) < 0, then $PG(\%) = 100\% \times$ (Mean $F_{test}$ − Mean $F_{time0}$)/(Mean $F_{time0}$ − Mean $F_{blank}$)

Where:

PG: percent growth

Mean $F_{time0}$ = The average of 2 measured fluorescent intensities of reduced alamarBlue at the time just before exposure of cells to the test substance.

Mean $F_{test}$ = The average of 2 measured fluorescent intensities of alamarBlue after 72-hour exposure of cells to the test substance.

Mean $F_{ctrl}$ = The average of 2 measured fluorescent intensities of alamarBlue after 72-hour incubation without the test substance.

Mean $F_{blank}$ = The average of 2 measured fluorescent intensities of alamarBlue in medium without cells after 72-hour incubation.

semi-quantitative $IC_{50}$, TGI and $LC_{50}$ were then determined by nonlinear regression using GraphPad Prism (GraphPad Software, USA).

IC50 (50% Inhibition Concentration): Test compound concentration where the increase from $time_0$ in the number or mass of treated cells was only 50% as much as the corresponding increase in the vehicle control at the end of experiment.

TGI (Total Growth Inhibition): Test compound concentration where the number or mass of treated cells at the end of experiment was equal to that at $time_0$.

LC50 (50% Lethal Concentration): Test compound concentration where the number or mass of treated cells at the end of experiment was half that at $time_0$.

B. Results

Figure 8:
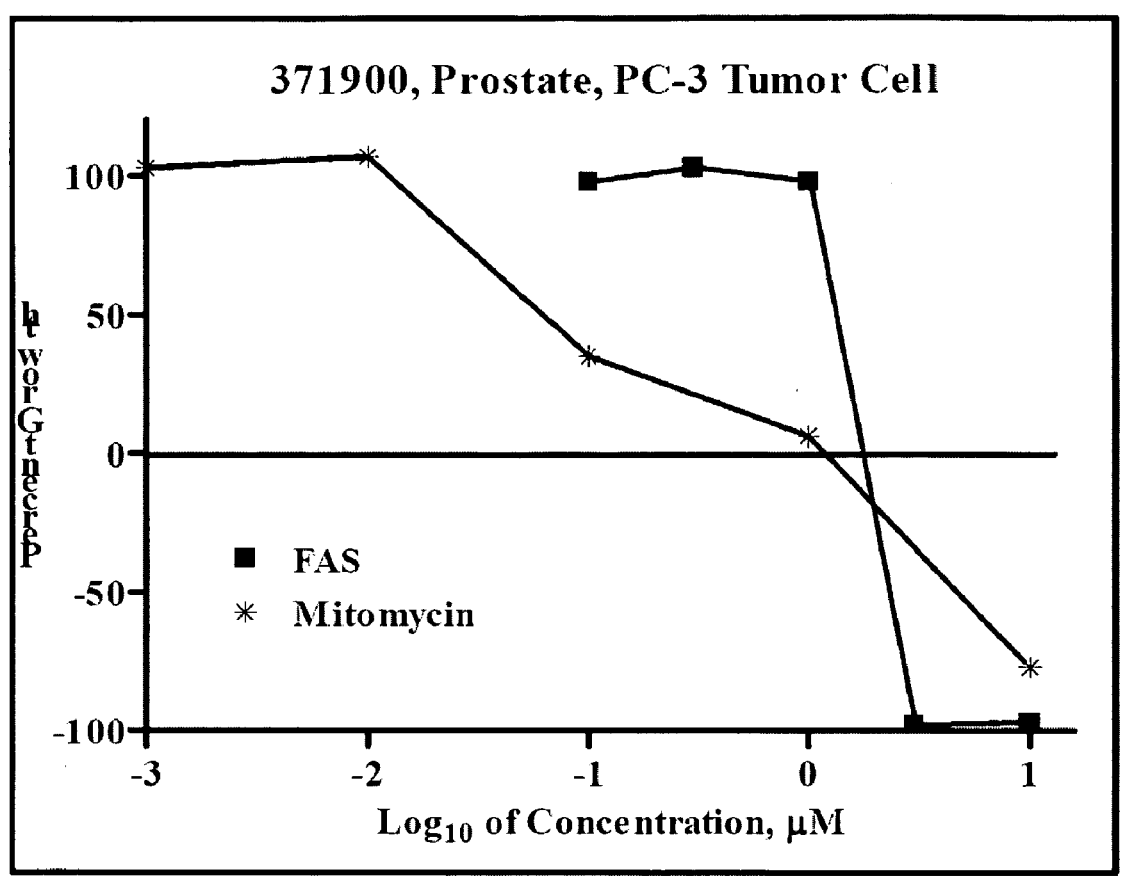
FIG. 8 shows the effect of frondoside A on growth of prostate cancer cells

The results are shown in Tables 3 and 4 and FIG. 8. Frondoside A caused significant growth inhibition ($\geq$50%) relative to the vehicle treated control group between 1 and 10 µM. Significant activity was also observed for the concurrently tested standard reference agent Mitomycin at <10 mM (Table 3 and FIG. 8). Semi-quantitative determinations of estimated $IC_{50}$ (50% inhibition concentration), TGI (total growth inhibition) and $LC_{50}$ (50% lethal concentration) values were calculated by nonlinear regression analysis and the results are shown in Table 4.

TABLE 3

Effect of Test Substances on Prostate, PC-3 Tumor Cell

| | | | | | Percent Growth (Mean ± SEM, n = 2) | | | | |
|---|---|---|---|---|---|---|---|---|---|
| | | | | | Concentration (µM) | | | | |
| Treatment | Assay Name | Blank | Time$_0$ | Vehicle | 10 | 3 | 1 | 0.3 | 0.1 |
| PT# 1031797-ADD (CBR-2) (FAS) | 371900, Prostate, PC-3 | −100 | 0 | 100 | −97 ± 1 | −98 ± 1 | 98 ± 3 | 103 ± 1 | 98 ± 3 |

| | | | | | Concentration (µM) | | | | |
|---|---|---|---|---|---|---|---|---|---|
| | | | | | 10 | 1 | 0.1 | 0.01 | 0.001 |
| Mitomycin | 371900, Prostate, PC-3 | −100 | 0 | 100 | −77 ± 2 | 6 ± 1 | 35 ± 0 | 107 ± 1 | 103 ± 1 |

A decrease of 50% or more ($\geq$50%) in fluorescent intensity relative to vehicle-treated control indicated significant cell growth inhibition, cytostatic or cytotoxic activity, and A decrease of 50% or more ($\geq$50%) in fluorescent intensity relative to vehicle-treated control indicates significant growth inhibition, cytostatic or cytotoxic activity.

TABLE 4

The Summary of $IC_{50}$, TGI and $LC_{50}$ Values

| Treatment | Assay # | Assay Name | [a]$IC_{50}$ | [b]TGI | [c]$LC_{50}$ |
|---|---|---|---|---|---|
| PT# 1031797-ADD (CBR-2) (FAS) | 371900 | Tumor, Prostate, PC-3 | 1.5 µM | 1.7 µM | 2.0 µM |
| Mitomycin | 371900 | Tumor, Prostate, PC-3 | 0.13 µM | 0.75 µM | 4.2 µM |

[a]$IC_{50}$ (50% Inhibition Concentration): Test compound concentration where the increase from $time_0$ in the number or mass of treated cells was only 50% as much as the corresponding increase in the vehicle-control at the end of experiment.
[b]TGI (Total Growth Inhibition): Test compound concentration where the number or mass of treated cells at the end of experiment was equal to that at $time_0$.
[c]$LC_{50}$ (50% Lethal Concentration): Test compound concentration where the number or mass of treated cells at the end of experiment was half that at $time_0$.

A semi-quantitative determination of $IC_{50}$, TGI and $LC_{50}$ was carried out by nonlinear regression analysis using GraphPad Prism (GraphPad Software, USA).

Example 4

Anti-Angiogenesis Activity of Frondoside A

This Example describes the anti-antigenic effect of Frondoside A.

Test Substance and Concentration. Frondoside A (CBR-24) was dissolved in 100% DMSO and then diluted with sterile distilled water to obtain initial working solutions of 1000, 300, 100, 30, and 10 µM in 40% DMSO. A 100-fold dilution was further made in culture media to generate final assay concentration of 10, 3, 1, 0.3 and 0.1 µM in 0.4% DMSO.

Cell Line and Culture Media. HUVEC (human umbilical vein endothelial cells), obtained from American Type Culture Collection (ATCC CRL-1730), were incubated in air atmosphere of 5% CO2 at 37° C. The culture medium used was Endothelial Cell Growth Medium with 10% fetal bovine serum, which was supplemented with 1% Antibiotic-Antimycotic.

Chemicals. Antibiotic-Antimycotic (GIBCO BRL, USA), Endothelial Cell Growth Medium (CELL APPLICATIONS, USA), Dimethylsulfoxide (Merck, Germany), Fetal Bovine Serum (HyClone, USA), Matrigel Matrix (BD Biosciences, USA) and Suramin (Sigma, USA).

Equipment. 96-microwell Tissue Culture Plate (NUNC, USA), $CO^2$ Incubator (Form a Scientific Inc., USA), Centrifuge 5810R (Eppendorf, Germany), Digital Camera (Nikon, Japan), Hemacytometer (Hausser Scientific Horsham, USA), Inverted Microscope CK-40 (Olympus, Japan), System Microscope E-400 (Nikon, Japan), and Vertical Laminar Flow (Tsao Hsin, R. O. C.).

Evaluation of anti-proliferation for test substances. Matrigel matrix was thawed, kept on ice at 4° C. and 50 µL transferred to each well of a 96-microwell tissue culture plate. The plate was incubated at 37° C. for at least one hour to allow the matrix solution to solidify before treatment.

Aliquots of 200 µl of (HUVEC) suspension (about 1.5× $10^4$ cells/well) were placed in 96-well microtiter plate. Two microliters of compound test solution or vehicle (40% DMSO) was then added per well in duplicate and incubated at 5% $CO_2$ at 37° C. for 18 hours. The final concentration of DMSO was 0.4%. The Frondoside A was evaluated for possible inhibitory effects on angiogenesis at concentrations of 100, 10, 1, 0.1 and 0.01 µM At the end of incubation, the morphology of endothelial cell tubes in each individual well was evaluated by photomicroscopy. Failure to form continuous networks between cell bodies in the presence of test substance was photographed and scored as to the extent of tube disruption at a magnification of 40×. Total tube length was measured from each picture and the significant inhibition ($\geqq 30\%$) was determined relative to the vehicle control group. The minimum inhibitory concentration (MIC) was calculated to assess the effect of the test substance on angiogenesis.

B. Results

Figure 9:
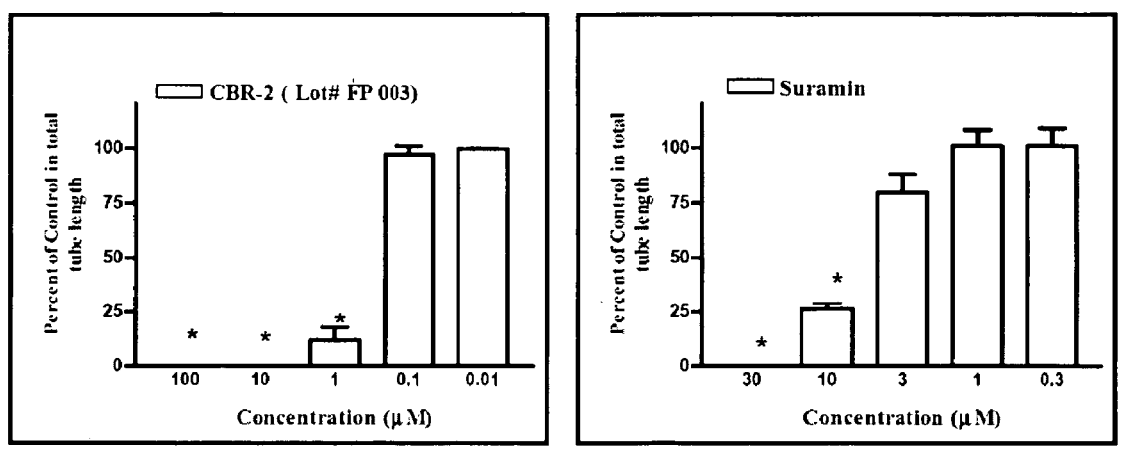
FIG. 9 shows the effect of frondoside A on angiogenesis.

Frondoside A at concentrations of 100, 10 and 1 µM caused significant inhibition ($\geqq 30\%$) of tube formation relative to the vehicle-treated controls. Similarly, significant inhibition is shown with the concurrently tested standard reference agent Suramin at 10 µM (Tables 5 and 6, FIG. 9).

TABLE 5

Effects of Test Substances against Angiogenesis Assay

%, Inhibition of the total tube length (Mean ± SEM, n = 2)

| Treatment | Assay Name | Concentration (µM) | | | | |
|---|---|---|---|---|---|---|
| | | 100 | 10 | 1 | 0.1 | 0.01 |
| PT# 1045143 (CBR-24) [CBR-2 (Lot # FP003)] | 368000, Angiogenesis, Tube Formation | 100 ± 0[a] | 100 ± 0[a] | 88 ± 6[a,b] | 3 ± 4 | 1 ± 1 |

| | | Concentration (µM) | | | | |
|---|---|---|---|---|---|---|
| | | 30 | 10 | 3 | 1 | 0.3 |
| Suramin | 368000, Angiogenesis, Tube Formation | 100 ± 0[a] | 74 ± 3[a,b] | 20 ± 8 | −1 ± 7 | −1 ± 8 |

[a]Significant inhibition of tube formation ($\geqq 30\%$)
[b]Minimum inhibitory concentration (MIC)

Inhibition of the tube formation for more than 30% relative to the vehicle-treated control indicates significant anti-angiogenic activity.

TABLE 6

Summary of Minimum Inhibitory Concentration (MIC)

| Treatment | Assay # | Assay Name | MIC |
|---|---|---|---|
| PT# 1045143 (CBR-24) [CBR-2 (Lot # FP003)] | 368000 | Tumor, Angiogenesis, Tube Formation | 1 µM |
| Suramin | 368000 | Tumor, Angiogenesis, Tube Formation | 10 µM |

Example 5

Anti-Angiogenesis Activity of Frondoside B

This Example describes the anti-antigenic effect of Frondoside B.

Test Substance and Concentration. Frondoside B is dissolved in 100% DMSO and then diluted with sterile distilled water to obtain initial working solutions of 1000, 300, 100, 30, and 10 µM in 40% DMSO. A 100-fold dilution is further made in culture media to generate final assay concentration of 10, 3, 1, 0.3 and 0.1 µM in 0.4% DMSO.

Cell Line and Culture Media. HUVEC (human umbilical vein endothelial cells), obtained from American Type Culture Collection (ATCC CRL-1730), is incubated in air atmosphere of 5% CO2 at 37° C. The culture medium used is Endothelial Cell Growth Medium with 10% fetal bovine serum, which is supplemented with 1% Antibiotic-Antimycotic.

Chemicals. Antibiotic-Antimycotic (GIBCO BRL, USA), Endothelial Cell Growth Medium (CELL APPLICATIONS, USA), Dimethylsulfoxide (Merck, Germany), Fetal Bovine Serum (HyClone, USA), Matrigel Matrix (BD Biosciences, USA) and Suramin (Sigma, USA).

Equipment. 96-microwell Tissue Culture Plate (NUNC, USA), $CO_2$ Incubator (Form a Scientific Inc., USA), Centrifuge 5810R (Eppendorf, Germany), Digital Camera (Nikon, Japan), Hemacytometer (Hausser Scientific Horsham, USA), Inverted Microscope CK-40 (Olympus, Japan), System Microscope E-400 (Nikon, Japan), and Vertical Laminar Flow (Tsao Hsin, R. O. C.).

Evaluation of anti-proliferation for test substances. Matrigel matrix is thawed, kept on ice at 4° C. and 50 µL transferred to each well of a 96-microwell tissue culture plate. The plate is incubated at 37° C. for at least one hour to allow the matrix solution to solidify before treatment.

Aliquots of 200 µl of (HUVEC) suspension (about 1.5× $10^4$ cells/well) are placed in 96-well microtiter plate. Two microliters of compound test solution or vehicle (40% DMSO) is then added per well in duplicate and incubated at 5% $CO_2$ at 37° C. for 18 hours. The final concentration of DMSO is 0.4%. The Frondoside B is evaluated for possible inhibitory effects on angiogenesis at concentrations of 100, 10, 1, 0.1 and 0.01 µM At the end of incubation, the morphology of endothelial cell tubes in each individual well is evaluated by photomicroscopy. Failure to form continuous networks between cell bodies in the presence of test substance is photographed and scored as to the extent of tube disruption at a magnification of 40×. Total tube length is measured from each picture and the significant inhibition ($\geq$30%) is determined relative to the vehicle control group. The minimum inhibitory concentration (MIC) is calculated to assess the effect of the test substance on angiogenesis.

B. Results

It is contemplated that Frondoside B at concentrations in the range of 1 µM and greater cause significant inhibition of tube formation relative to the vehicle-treated controls.

Example 6

Treatment of Animals

Frondoside A or B is evaluated for anti-angiogenic (e.g., for research, drug screening or therapeutic purposes) in live animals. Animals (e.g., having or modeling a disease characterized by unwanted angiogenesis) are treated with a range of appropriate doses of Frondoside A or B. Exemplary dosages and dosage schedules include, but are not limited to, those described herein. It is contemplated that the administration of Frondoside A or B inhibits angiogenesis in the animal.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method for reducing cellular proliferation comprising the step of exposing said cells to a frondoside selected from the group consisting of *Cucumaria frondosa* Frondoside A and *Cucumaria frondosa* Frondoside B.

2. The method of claim 1, wherein said cellular proliferation is associated with cancer.

3. The method of claim 1, wherein said cells are located in vivo in a subject.

4. The method of claim 2, wherein said cancer is selected from the group consisting of pancreatic cancer, colon cancer, breast cancer, skin cancer and prostate cancer.

5. The method of claim 3, wherein said subject is a human.

6. The method of claim 1, wherein said Frondoside compound is obtained from a natural source.

7. The method of claim 1, wherein said cells are further exposed to a second compound having anti-proliferative properties.

8. The method of claim 7, wherein said second compound is a known cancer chemotherapeutic agent.

9. A therapeutic composition comprising a Frondoside compound selected from the group consisting of *Cucumaria frondosa* Frondoside A and *Cucumaria frondosa* Frondoside B, wherein said frondoside is configured for administration to a subject having or suspected of having cancer.

10. The composition of claim 9, wherein said composition further comprises a second anti-proliferative compound.

11. The composition of claim 10, wherein said second compound is a known cancer chemotherapeutic agent.

12. The composition of claim 9, wherein said cancer is selected from the group consisting of pancreatic cancer, colon cancer, skin cancer and prostate cancer.

13. The composition of claim 9, wherein said subject is a human.

14. The composition of claim 9, wherein said Frondoside compound is obtained from a natural source.

15. The composition of claim 9, wherein said frondoside is formulated as a pharmaceutical composition.

* * * * *